(12) United States Patent
Andrelczyk et al.

(10) Patent No.: US 8,808,639 B2
(45) Date of Patent: *Aug. 19, 2014

(54) TEST STRIP CARD

(71) Applicant: Akers Biosciences, Inc., Thorofare, NJ (US)

(72) Inventors: Susan Andrelczyk, West Deptford, NJ (US); Leonard Schluter, Blackwood, NJ (US)

(73) Assignee: Akers BioSciences, Inc., Thorofare, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/847,651

(22) Filed: Mar. 20, 2013

(65) Prior Publication Data

US 2013/0217042 A1   Aug. 22, 2013

Related U.S. Application Data

(63) Continuation of application No. 13/170,838, filed on Jun. 28, 2011, now Pat. No. 8,425,859, which is a continuation of application No. 10/842,000, filed on May 6, 2004, now Pat. No. 8,003,061.

(51) Int. Cl.
*G01N 21/78* (2006.01)

(52) U.S. Cl.
CPC ................ *G01N 21/78* (2013.01)
USPC ........... 422/409; 422/419; 422/420; 422/425; 436/165; 436/169

(58) Field of Classification Search
CPC .............. G01N 21/78; G01N 21/80
USPC ............. 422/401, 408, 409, 419, 420, 425; 436/165, 169

See application file for complete search history.

(56) References Cited

U.S. PATENT DOCUMENTS

| | | | |
|---|---|---|---|
| 1,389,836 A | 9/1921 | Mooney |
| 1,967,557 A | 7/1937 | John |
| 4,523,852 A | 6/1985 | Bauer |
| 4,797,256 A | 1/1989 | Watlington, IV |
| 4,877,580 A | 10/1989 | Aronowitz et al. |
| 5,595,187 A | 1/1997 | Davis |
| 6,184,040 B1 | 2/2001 | Polizzotto et al. |
| 6,284,550 B1 | 9/2001 | Carroll et al. |
| 6,377,894 B1 | 4/2002 | Deweese et al. |
| 8,003,061 B2 | 8/2011 | Andrelczyk et al. |
| 8,425,859 B2 | 4/2013 | Andrelczyk et al. |
| 2004/0156037 A1 | 8/2004 | Mawhirt et al. |

FOREIGN PATENT DOCUMENTS

WO   2005108976   11/2005

OTHER PUBLICATIONS http://www.visualillusion.net/Chap10/Page02.php.
Office Action issued Sep. 25, 2005 in U.S. Appl. No. 10/842,000 by Andrelczyk.

(Continued)

*Primary Examiner* — Paul Hyun
(74) *Attorney, Agent, or Firm* — Panitch Schwarze Belisario & Nadel LLP

(57) ABSTRACT

The present invention relates to a test strip for determining and/or quantifying a property of a sample, such as the concentration of an analyte, the pH, the viscosity, or the specific gravity of a fluid specimen. More particularly, the present invention relates to an improved test strip and scale for determining and/or quantifying a property of a sample, such as the concentration of an analyte, the pH, the viscosity, or the specific gravity of a fluid specimen.

13 Claims, 1 Drawing Sheet

(56) References Cited

OTHER PUBLICATIONS

Office Action issued Feb. 9, 2006 in U.S. Appl. No. 10/842,000 by Andrelczyk.
Office Action issued Aug. 22, 2006 in U.S. Appl. No. 10/842,000 by Andrelczyk.
Office Action issued Apr. 3, 2007 in U.S. Appl. No. 10/842,000 by Andrelczyk.
Office Action issued Nov. 13, 2007 in U.S. Appl. No. 10/842,000 by Andrelczyk.
Office Action issued May 19, 2008 in U.S. Appl. No. 10/842,000 by Andrelczyk.
Office Action issued Mar. 6, 2009 in U.S. Appl. No. 10/842,000 by Andrelczyk.
Office Action issued Sep. 30, 2009 in U.S. Appl. No. 10/842,000 by Andrelczyk.
Office Action issued Jan. 21, 2010 in U.S. Appl. No. 10/842,000 by Andrelczyk.
Office Action issued Sep. 1, 2010 in U.S. Appl. No. 10/842,000 by Andrelczyk.
Office Action issued Dec. 23, 2011 in U.S. Appl. No. 13/170,838 by Andrelczyk.
Office Action issued Aug. 17, 2012 in U.S. Appl. No. 13/170,838 by Andrelczyk.

TEST STRIP CARD

The present application is a continuation of U.S. patent application Ser. No. 13/170,838, filed on Jun. 28, 2011, which has issued as U.S. Pat. No. 8,425,859, which is a continuation of U.S. patent application Ser. No. 10/842,000, filed on May 6, 2004, which has issued as U.S. Pat. No. 8,003,061, the entire contents of which are hereby expressly incorporated herein by reference thereto.

FIELD OF THE INVENTION

The present invention relates to a test strip for determining and/or quantifying a property of a sample, such as the concentration of an analyte, the pH, the viscosity, or the specific gravity of a fluid specimen. More particularly, the present invention relates to an improved test strip and scale for determining and/or quantifying a property of a sample, such as the concentration of an analyte, the pH, the viscosity, or the specific gravity of a fluid specimen.

BACKGROUND OF THE INVENTION

Test strips on which a fluid specimen is dropped, or which are dipped into a fluid specimen, are known in the art. The test strip has a sample pad, on which the sample or specimen is received, and a reagent pad with a reaction zone carrying a reagent. The sample is received on the sample pad and migrates from there to the reaction pad. On the reaction pad, the sample and a reagent on the reaction pad undergo a reaction. Such a reaction can be, e.g., a colorimetric reaction or a reaction that changes the light reflection properties of the reaction pad. The reagent pad may be coextensive with the sample pad, or spaced from the sample pad so that the specimen migrates from the sample pad to the reagent pad. The sample may also be placed directly onto the reaction pad. Once the fluid specimen reacts with the reagent in the strip, the reagent pad (in a reaction zone of the reagent pad) changes its light reflection and/or absorption pattern, which may be perceived as a change of color and/or brightness. The test strip is then carried to a comparison scale where the reagent pad is compared with the scale. Typically, the comparison scale is a color scale, and the color of the reagent pad is aligned with the substantially identical color on the comparison scale to determine the quantity of the component in question in the fluid sample, or the presence of a particular component in the fluid sample, or another characteristic or property of the fluid sample. Such components and characteristics include for example, the pH of a liquid, the concentration of certain ions, the presence of certain microorganisms in the sample, temperature, the concentration of certain biomolecules (such as sugars, DNA, RNA, lipids, proteins, peptides and amino acids) and/or the concentration of small organic or inorganic molecules or other analytes.

Because the test strip has to be carried to a color scale, the doctor, nurse, technician, or tester must handle the strip not only to apply the fluid specimen thereto, but also to manipulate the test strip with respect to the color scale. Such additional handling is generally undesirable for efficiency as well as hygienic reasons, yet has been heretofore essentially unavoidable. Moreover, the test strip is generally a rather thin, flimsy piece of paper or the like and can easily be blown over or otherwise inadvertently moved to an undesired location by, for example, a breeze of air.

Therefore, it would be desirable to reduce the amount of handling required to utilize a test strip for measuring the presence or amount of a component in question. Moreover, it would be desirable to modify the test strip so that it is not easily displaced.

SUMMARY OF THE INVENTION

In accordance with the principles of the present invention, a test strip is coupled to a test scale card on which a test scale is provided. The test scale comprises a comparison scale. Optionally, the test scale further comprises a reading scale. The test strip has a reagent pad with a reaction zone. The reaction zone is the area of the reagent pad where the reaction between the sample that is to be tested and a reagent takes place. The reaction zone can be coextensive with the reaction pad, or, alternatively, the reaction zone can be a part of the reaction pad. The reaction results in a visual signal in the reaction zone. The reaction zone of the test strip is positioned adjacent the comparison scale so that the test strip may be moved or slid along the comparison scale to align the reaction zone with the matching visual value or zone (hereinafter "level" for the sake of convenience) on the comparison scale of the test scale. The user thus can readily determine a property, such as the concentration of an analyte, the pH, the viscosity or the specific gravity, of the specimen dropped on the test strip (or in which the test strip was dipped) upon comparison of the reagent pad with the comparison scale and reading the corresponding value on the reading scale.

In one embodiment, the test strip is slidable in a pocket in the test scale card with the reaction zone of the test strip visible through a window (e.g., a slot) in the test scale card. The comparison scale is provided along the window so that movement of the test strip moves the reaction zone into alignment with the matching level along the comparison scale so that a match and thus an appropriate reading may be achieved with ease.

The test strip preferably is readily accessible to the user so the user may readily move the test strip with respect to the test scale card. For instance, the test strip may extend slightly beyond the edge of the test scale card. Alternatively, a portion of the test strip may be accessible through the test scale card. For instance, a notch may be provided at an end of the test scale card to expose a pull end, such as a pull tab section, of the test strip.

BRIEF DESCRIPTION OF THE DRAWINGS

The present invention can be better understood by reference to the following drawings, wherein like references numerals represent like elements. The drawings are merely exemplary and the present invention is not limited to the embodiments shown.

DETAILED DESCRIPTION OF THE INVENTION

Figure 1:
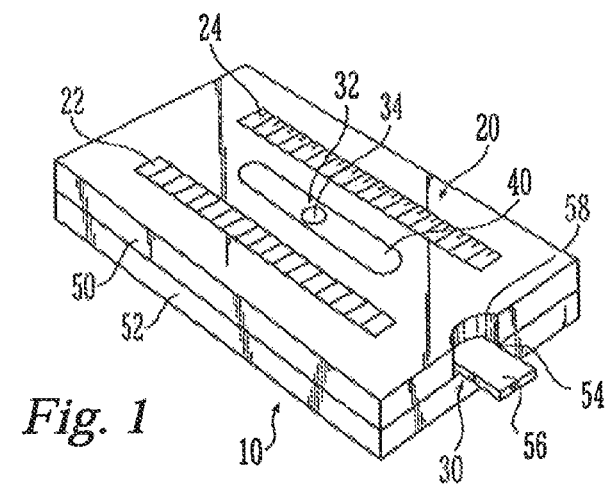
FIG. 1 is a top perspective view of an exemplary sliding test strip in accordance with the principles of the present application.

As illustrated in FIG. 1, exemplary test strip card 10, formed in accordance with the principles of the present invention, has test scale card 20 on which comparison scale 22 and reading scale 24 are provided and to which a test strip 30 is movably coupled. Test strip 30 has a reagent pad 32 with reaction zone 34 that reacts with a specimen, such as a fluid specimen, applied to test strip 30, as described in further detail below. Reaction zone 34 is the area of reagent pad 30 where the reaction between the sample that is to be tested and a reagent takes place, as described in further detail below. The reaction results in a visual signal in reaction zone 34. Test strip 30 is movably coupled to test scale card 20 to move reagent pad 32 or at least reaction zone 34 along comparison scale 22 to align reaction zone 34 with a matching level along comparison scale 22.

Thus, test strip card 10 permits a specimen to be applied to a test strip and for the test strip to be "read" with a single, combined testing device. Individual exemplary components of test strip card 10 and their exemplary functions will now be described in greater detail.

Test scale card 20 preferably is formed from a sufficiently rigid or stiff enough material so that test scale card 20 has structural stability and remains relatively stiff and flat without external support (an element with such structural stability is described hereinafter as "self-supporting" for the sake of convenience). For instance, test scale card 20 may be formed from heavy-weight paper, paperboard, lightweight cardboard, or plastic. For the sake of economy, the thickness of such material is selected to be as thin as possible while still permitting test scale card 20 to be self-supporting. Thus, material use is minimized, and more test strip cards can fit in the same amount of space (thus facilitating sale and storage of large quantities). Alternatively, a relatively flimsy material may be used to form test scale card 20 (such that test scale card 20 is not self-supporting) and an additional support may be provided so that test strip card 10 is self-supporting.

Test strip 30 may be movably coupled to test scale card 20 in any of a number of manners. For instance, test scale card 20 may be in the form of a sleeve or double-walled element with a pocket therebetween in which test strip 30 is movably or slidably positioned. Reagent pad 32, or at least reaction zone 34, is visible through window 40 in test scale card 20 along which comparison scale 22 is provided. Window 40 may be an open window for the sake of simplicity. However, if it is desired to protect reaction zone 34 from contaminants (such as dust), a transparent material (e.g., plastic) may be fitted in window 40.

As illustrated in FIG. 1, test scale card 20 may be formed with a front wall 50 and a back wall 52 coupled together to form a pocket 54 therebetween in which test strip 30 is movably or slidably positioned. A pull end 56 of test strip 30 may extend beyond the borders of test scale card 20 so that a user may access and move test strip 30 with respect to test scale card 20. If desired, a notch 58 may be formed in one or both of walls 50, 52 to access pull end 56 of test strip 30 so that pull end 56 need not extend beyond the borders of test scale card 20. Thus, test strip 30 is readily accessible by a user to move reaction zone 34 into aliment with the matching level along comparison scale 22.

Figure 2:
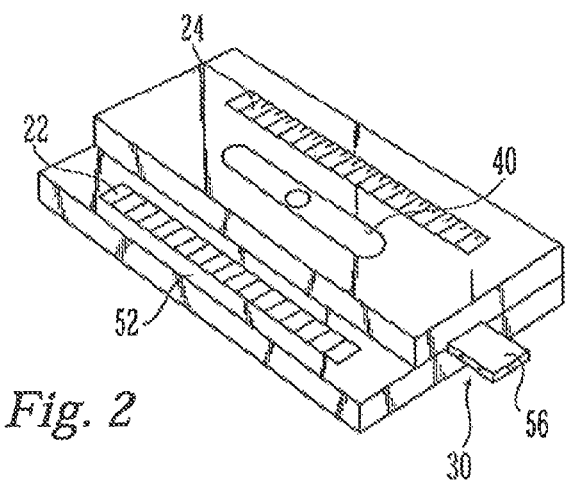
FIG. 2 is a top perspective view of another exemplary sliding test strip in accordance with the principles of the present application.

Front wall 50 and back wall 52 may be formed separately and coupled together in any desired manner to form a single-piece test scale card 20. Alternatively, front wall 50 and back wall 52 may be formed from a single piece of material folded (e.g., in half) to form a double-walled test scale card. If desired, front wall 50 and back wall 52 may have different dimensions. For example, back wall 52 may be larger than front wall 50 and comparison scale 22 may be provided along the portion of back wall 52 visible when front wall 50 is coupled to back wall 52 (such as by aligning two adjacent edges or borders of front wall 50 with two adjacent edges or borders of back wall 52), as illustrated in FIG. 2.

Comparison scale 22 and reading scale 24 may be printed directly on front wall 50, or may be formed on a separate piece of material affixed (e.g., adhered) to front wall 50 of test strip card 10. Comparison scale 22 may be a "color" chart having a variety of different colors or varying shades or hues or tints (herein, these terms are understood as interchangeable) of a single color. In certain embodiments, the scale is a scale of different degrees of brightness or different grey values. Any other type of scale may be used instead.

In certain embodiments, the comparison scale comprises a continuous scale of levels on the comparison scale, such as a continuous scale of colors, or a series of fields, each field encompassing different visual information, i.e., different levels, such as a different color. In certain embodiments, a reading scale of the comparison scale consists of a series of numerical values that are printed next to the continuous scale of levels or the different fields of the comparison scale. The numerical values and the levels are matched such that a level or a range of levels corresponds to a numerical value. In more specific embodiments, the numerical value is the quantified property in the sample being tested. The property to be tested can be the concentration of an analyte, the pH, the viscosity, or the specific gravity of the sample. The test strip and the comparison scale are calibrated such that if the level on the test strip matches with a level in the comparison scale, the concentration of the component being tested is the numerical value on the reading scale that corresponds to the matching level on the comparison scale.

The sample can be applied to the test strip, i.e., to the sample pad or directly on the reaction pad, by any method known to the skilled artisan. In certain embodiments, the sample is dropped on the sample pad or directly on the reaction pad. In certain, more specific embodiments, the sample is placed onto the test strip using a pipette. In certain embodiments, the test strip is placed directly into the sample. In certain embodiments, the sample pad is made from an absorbent material. If the material is not directly applied to the reaction pad, the sample can migrate from the sample pad to the reaction pad. In certain embodiments, the sample pad, the reagent pad, and the reaction zone are attached to a solid support, wherein the solid support is less absorbent than the sample pad and the reagent pad. The reagent pad is impregnated with a reagent that can react with and/or bind to the component of which the presence or the concentration is to be determined. The reaction and/or binding takes place at the reaction zone. The reaction or binding between the component and the reagent results in a change of the optical properties of the reagent and the light absorption/reflection spectrum of the reagent pad changes at the reaction zone.

Any test strip known to those of ordinary skill in the art for performing the desired tests and produce accurate easily detectable results may be used. A variety of different test strips for determining or detecting various properties or characteristics are known, as described below, and may be used in test strip card 10 of the present invention.

In certain embodiments, the test strip of the present invention can be used to measure total and high-density lipoprotein (HDL) cholesterol concentration. Blood cholesterol levels are directly related to the risk of cardiovascular disease. The HDL and Total Cholesterol rapid assays provide semi-quantitative determinations of high-density lipoprotein (HDL) cholesterol and total cholesterol levels in whole blood obtained from a finger stick. The tests have been designed in a strip format; and an enzymatic color reaction from a single drop of blood can produce results in approximately three minutes. The strip may contain a sandwich of membranes that perform the following functions: separation of blood cells from serum, collection of serum, reaction of serum with cholesterol oxidase and substrate, and substrate color formation. The membrane sandwich may be assembled in such a way that the whole blood sample is applied to the surface of the separator membrane, and the serum produced moves vertically through the sandwich contacting the reagents in successive layers. The substrate color is formed on the bottom layer of the sandwich.

In certain embodiments, the test strip of the present invention can be used to determine the concentration of glucose in a sample. Determination of blood glucose levels are important in the diagnosis and management of diabetes. The glucose rapid assay provides semi-quantitative determinations of glucose levels in whole blood obtained from a finger stick. The test may be designed in a strip format; and an enzymatic color reaction from one or more drops of blood can produce a result in approximately three minutes. The strip may contain a sandwich of membranes that perform the following functions: separation of blood cells from serum, collection of serum, reaction of serum with glucose oxidase and substrate, and substrate color formation. The membrane sandwich may be assembled in such a way that the whole blood sample is applied to the surface of the separator membrane, and the serum produced moves vertically through the sandwich contacting the reagents in successive layers. The substrate color is formed on the bottom layer of the sandwich.

In certain embodiments, the test strip can be used to determine the pH in a sample. For instance, urinary pH levels are important in the diagnosis of disease states and nutritional deficiencies. The urine pH rapid assay provides semi-quantitative determinations of pH directly from a drop of urine. The test may be designed in a strip format; and a color reaction from a single drop of urine can produce results immediately. The strip may contain a sandwich of membranes that perform the following functions: separation of urinary precipitates or debris, and reaction of the urine with a test strip producing color formation. The membrane sandwich may be assembled in such a way that the urine sample is applied to the surface of the separator membrane, and the filtered urine produced moves vertically through the sandwich contacting the test strip. The color is formed on the bottom layer of the sandwich.

In certain specific embodiments, a test strip in accordance with U.S. Pat. No. 4,774,192, issued Sep. 27, 1988 to Terminiello et al., and U.S. Pat. No. 4,877,580, issued Oct. 31, 1989 to Aronowitz et al., both of which are incorporated herein by reference in their entirety, may be used.

Certain other exemplary tests for the quantification of glucose or protein or determining the pH that may be used in the present invention are described in U.S. Pat. No. 5,178,831, issued Jan. 12, 1993 to Sakota et al. (see, e.g., section entitled "Test Reagent Layer"), which is incorporated herein by reference in its entirety.

Figure 3:
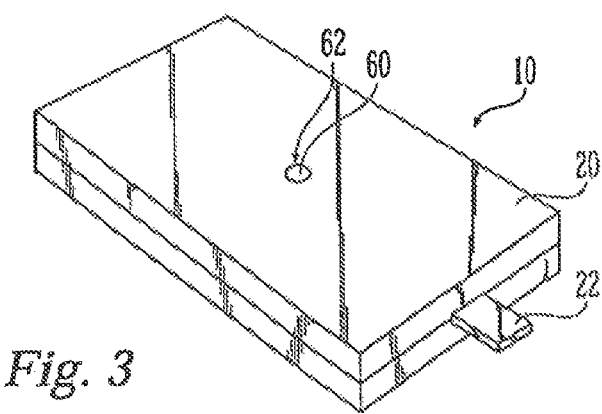
FIG. 3 is a bottom perspective view of an exemplary sliding test strip in accordance with the principles of the present application.

In one embodiment, the fluid specimen is dropped onto a sample pad 60 on the back surface of test strip 22, as illustrated in FIG. 3. Preferably, for the sake of convenience, sample pad 60 is accessible through an application window 62 through back wall 52 of test scale card 20. Alternatively, test strip 30 may be withdrawn from test scale card 20 so that the specimen may be applied to sample pad 60. In one embodiment, the sample pad separates those components in the sample that interfere with the reaction and retains them. For instance, the sample pad may retain blood cells so that only serum passes to the reagent pad, and red blood cells will not alter a color change that occurs upon reaction of the sample with the reagent. The specimen then migrates to reaction zone 34 on the reagent pad 32 and the reaction zone 34 changes its optical properties. In certain embodiments, reaction zone 34 and reagent pad 32 are coextensive with each other such that the entire reagent pad changes its optical properties.

In certain embodiments, reagent pad 32 has a plurality of layers, wherein one of the layers is reaction zone 34. While the sample migrates through the different layers of reagent pad 32, the sample or a component of the sample can undergo one or more reactions. However, the visual signal that is being compared with comparison scale 22 results from the contact between the sample and reaction zone 34.

The test strip cards are packaged in kits containing finger stick devices and all other necessary accessories, making them ideal for office or home use.

It will be appreciated that the scope of the invention is not limited to the embodiment illustrated in the figures and that the principles of the present invention are broader than such embodiment. For instance, the present invention encompasses a test strip card having more than one test strip and more than one comparison scale. In one embodiment, a test strip card formed in accordance with the principles of the present invention may be formed to test cholesterol levels in a patient's blood sample. Thus, a first test strip and comparison scale may be provided to measure HDL cholesterol levels in the blood sample, and a second test strip and comparison scale may be provided to measure total cholesterol level in the blood sample.

Additionally, it will be appreciated that the positions of any of the comparison scale, test strip, and window may be modified from the locations illustrated. For instance, the test strip may be along a side edge and the comparison scale provided on the side edge of the test scale card.

Accordingly, while the foregoing description and drawings represent embodiments of the present invention, it will be understood that various additions, modifications and substitutions may be made therein without departing from the spirit and scope of the present invention as defined in the accompanying claims. In particular, it will be clear to those skilled in the art that the present invention may be embodied in other specific forms, structures, arrangements, proportions, and with other elements, materials, and components, without departing from the spirit or essential characteristics thereof. One skilled in the art will appreciate that the invention may be used with many modifications of structure, arrangement, proportions, materials, and components and otherwise, used in the practice of the invention, which are particularly adapted to specific environments and operative requirements without departing from the principles of the present invention. The presently disclosed embodiments are therefore to be considered in all respects as illustrative and not restrictive, the scope of the invention being indicated by the appended claims, and not limited to the foregoing description.

What is claimed:

1. A test strip card for testing a property of a fluid specimen, said test strip card comprising:

a comparison scale that comprises a continuous scale of visual levels;

a test strip having (a) a reaction zone which is a part of a reagent pad where a fluid specimen reacts with a reagent, and (b) a zone that is not part of the reaction zone which does not optically change when the fluid specimen reacts with the reagent, the test strip being movably coupled to said test strip card for performing a reaction on the reaction zone on the reagent pad of the test strip; and a window along said comparison scale for viewing (a) the reaction zone of the test strip and (b) at least a portion of the zone of the test strip that is not part of the reaction zone, wherein said test strip is movable with respect to said comparison scale to align said reaction zone with a matching visual level on said comparison scale thereby indicating the property of the specimen.

2. The test strip card of claim 1, wherein:
said test strip card further comprises a front wall, a back wall, and a pocket between said front wall and said back wall; and
said test strip is movably located within said pocket in said test strip card.

3. The test strip card of claim 2, wherein:
said window is formed in said front wall along said comparison scale; and part of said reaction zone on said test strip is visible through said window along said comparison scale.

4. The test strip card of claim 2, wherein said test strip has a pull end extending beyond the borders of said front wall and said back wall.

5. The test strip card of claim 2, wherein; a notch is defined at an end of at least one of said front wall and said back wall; and said test strip has a pull end accessible through said notch.

6. The test strip card of claim 2, wherein said test strip has a front side adjacent said front wall of said test strip card and on which said reaction zone is positioned, and a back side adjacent said back wall of said test strip card and carrying a sample pad, wherein the sample is administered to said sample pad.

7. The test strip card of claim 1, wherein said comparison scale comprises a spectrum or series of visual levels selected from the group consisting of colors, hues, shades, and tints.

8. The test strip card of claim 7, further comprising a reading scale aligned with said comparison scale and including a series of numerical values that are matched with the different visual levels of said comparison scale.

9. The test strip of claim 1, wherein said property is the concentration of an analyte.

10. The test strip of claim 9, wherein the analyte reacts with or binds to a reagent in the reaction zone, and wherein the binding or reaction between the analyte and the reagent results in a change of the optical properties of said reaction zone.

11. The test strip of claim 1, wherein the property is the viscosity, the pH, or the specific gravity of the liquid specimen.

12. The test strip card of claim 1, wherein the window is positioned adjacent said comparison scale and extends along a plurality of the visual levels, and wherein said test strip is movable with respect to said window.

13. A test strip card for testing a property of a fluid specimen, said test strip card comprising:
a comparison scale that comprises a continuous scale of visual levels;
a test strip having (a) a reaction zone which is a part of a reagent pad where a fluid specimen reacts with a reagent, and (b) a zone that is not part of the reaction zone, the test strip being movably coupled to said test strip card for performing a reaction on the reaction zone on the reagent pad of the test strip; and
a window along said comparison scale for viewing (a) the reaction zone of the test strip and (b) at least a portion of the zone of the test strip that is not part of the reaction zone,
wherein said test strip is movable with respect to said comparison scale to align said reaction zone with a matching visual level on said comparison scale thereby indicating the property of the specimen,
wherein the window is positioned adjacent said comparison scale and extends along a plurality of the visual levels, and
wherein said test strip is movable with respect to said window.

* * * * *